United States Patent [19]

Blank et al.

[11] 4,012,442
[45] Mar. 15, 1977

[54] PROCESS FOR PREPARING M-CHLOROBENZENE SULPHONYL CHLORIDE

[75] Inventors: Heinz-Ulrich Blank, Odenthal-Globusch; Karlfried Wedemeyer, Cologne, both of; Josef Ebersberger, deceased, late of Bergen, Germany, by Thea Ebersberger, heiress

[73] Assignee: Bayer Aktiengesellschaft, Leverkusen, Germany

[22] Filed: Mar. 17, 1975

[21] Appl. No.: 559,272

Related U.S. Application Data

[62] Division of Ser. No. 465,649, April 30, 1974, Pat. No. 3,897,321.

[30] Foreign Application Priority Data

May 24, 1973 Germany ............................ 2326414

[52] U.S. Cl. ............................................. 260/543 R
[51] Int. Cl.$^2$ ......................................... C07C 143/70
[58] Field of Search ............................... 260/543 R

[56] References Cited
OTHER PUBLICATIONS

Olah, "Friedi–Crafts and Related Reactions," vol. III, p. 1549 vol. IV, pp. 112–114 (1965) Interscience Publishers, New York, N.Y.

Primary Examiner—Norman Morgenstern
Attorney, Agent, or Firm—Burgess, Dinklage & Sprung

[57] ABSTRACT

Meta-chlorobenzene sulphonyl chloride and metadichlorobenzene are prepared by reacting benzene sulphonyl chloride with chlorine in the presence of a Friedel-Crafts catalyst at a temperature of from 0° to 150° C. After removing the catalyst, the resulting m-chlorobenzene sulphonyl chloride is reacted to form m-dichlorobenzene. The m-chlorobenzene sulphonyl chloride is preferably isolated prior to being reacted to m-dichlorobenzene. The reaction forming m-dichlorobenzene can be carried out via thermal clevage, thermal chlorolysis or chlorolysis initiated photochemically or by radicals.

5 Claims, No Drawings

PROCESS FOR PREPARING M-CHLOROBENZENE SULPHONYL CHLORIDE

This is a division of application Ser. No. 465,649, filed Apr. 30, 1974, now U.S. Pat. No. 3,897,321.

BACKGROUND

The invention relates to a process for the production of m-chlorobenzene sulphonyl chloride and m-dichlorobenzene.

SUMMARY

More particularly, the invention relates to a particularly advantageous process for the production of m-chlorobenzene sulphonyl chloride and m-dichlorobenzene, having the characteristic feature that benzenesulphonyl chloride is reacted in the presence of Friedel-Crafts catalysts at a temperature in the range of from −20° to 180° C with chlorine, and the resulting m-chlorobenzene sulphonyl chloride, after removal of the catalyst and optionally after intermediate separation, is optionally reacted in the presence of chlorinating agents to form m-dichlorobenzene.

In the first stage of the process, it is preferably to work at 10° to 150° C, more particularly at 20° to 100°c.

The invention also provides a process for the production fo m-chlorobenzene sulphonyl chloride, in which benzene sulphonyl chloride is reacted with chlorine in the presence of a Friedel-Crafts catalyst at a temperature of from 0° to 150° C.

tity of dry chlorine is introduced until all the benzene sulphonyl chloride is reacted. So as to avoid secondary reactions, it may be expedient to chlorinate only up to a conversion of from 10 to 95% (advantageously from 50 to 90%) and once again to introduce unreacted benzene sulphonyl chloride after isolation. In the case of the practically complete chlorination, the introduced quantity of chlorine amounts to 1 to 5 mols, advantageously 1.0 to 2.5 mols, per mol of reacted benzene sulphonyl chloride. The progress of the reaction is preferably monitored by weighing or gas chromatography. When working with an excess of chlorine, any unreacted chlorine is recovered, for example, by condensation and is returned to the reaction or supplied to a second chlorination batch. After removing the Friedel-Crafts catalyst, the m-chlorobenzene sulphonyl chloride which has formed can be directly reacted, optionally after intermediate isolation, to form m-dichlorobenzene, for example by the following methods:

a. Thermal cleavage

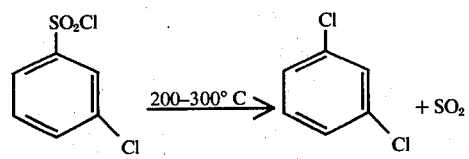

The reaction optionally takes place with simultaneous ultraviolet radiation.

b. Thermal chlorolysis

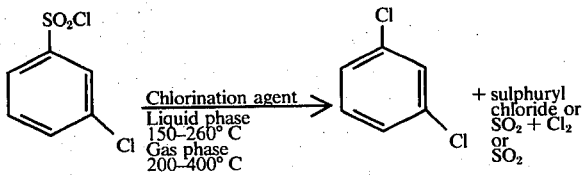

DESCRIPTION

As Friedel-Crafts catalysts, the following may for example be used: iodine, SbCl$_3$, SbCl$_5$, AlCl$_3$, TlCl, Fe, Fe/I$_2$, Fe/S$_x$Cl$_2$ ($x = 1$ or $>1$, preferably 1 to 5), Fe/S, FeCl$_3$ and Fe$_2$O$_3$. Catalysts which contain iron and antimony are preferably used. The catalyst is employed in quantities of from 0.01 to 10% by weight and preferably 0.1 to 6.0% by weight, relative to benzene sulphonyl chloride.

It is also possible to work in the presence of those inert diluents which are commonly used with halogenation reactions, so as, for example, to produce a better dissipation of heat. The following are mentioned as examples of diluents: carbon tetrachloride, tetrachlorethane, perchlorethylene, glacial acetic acid and petroleum ether.

The benzene sulphonyl chlorides used for the reaction are obtainable by known processes. No particular standards of purity are required for these starting compounds. The degree of purity of technically produced benzene sulphonyl chloride is adequate for carrying out the process according to the invention.

Generally speaking, in the first stage of the process, optionally after previous saturation of the reaction mixture with hydrogen chloride gas, a sufficient quan- Chlorination agents include PCl$_5$, POCl$_3$ and thionyl chloride, and the like, preferably chlorine and sulphuryl chloride. The quantity of chlorinating agent used amounts to 0.1 to 5 mol and advantageously 1.0 to 2.0 mols, based on 1 mol of m-chlorobenzene sulphonyl chloride.

c. Chlorolysis initiated photochemically or by radicals

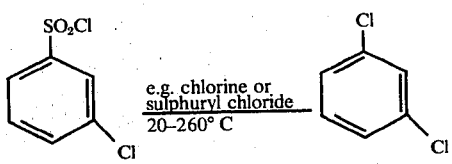

The operation is here carried out with ultraviolet irradiation (e.g. quartz lamp), and 0.1 to 5, advantageously 1.0 to 2.0 mols of chlorinating agent, advantageously chlorine or sulphuryl chloride, are used for each mol of m-chlorobenzene sulphonyl chloride. The use of radical formers, as for example azo-bis-isobutylonitrile or peroxides, such as benzoyl peroxide, in amounts of from 0.1 to 5% by weight, based on m-chlorobenzene sulphonyl chloride, can also be advantageous.

With the processes (a) to (c), large variations in the reaction conditions are possible. At temperatures higher than approximately 180° C, the reaction can, for example, proceed simultaneously according to the variants (a) to (c). The methods (a) to (c) are generally carried out in the liquid phase at temperatures of from 20° C to 300° C or in the gaseous phase at temperatures of from 200° to 400° C, and at pressures of from 1 mm.Hg to several atmospheres.

When working in the liquid phase in the upper temperature range, the preferred form of reaction is thermal chlorolysis (b), using chlorine or sulphuryl chloride in the temperature range of from 150° to 260° C, more especially 180° to 230° C, possibly under reduced or slightly raised pressure, but advantageously under normal pressure.

The thermal cleavage (a) is preferably carried out at 200° to 260° C and with simultaneous ultraviolet irradiation. If the thermal cleavage (a) is carried out in the liquid phase, then in the same way as with the thermal chlorolysis (b), the operation preferably takes place at the boiling point of the reaction mixture. The reaction temperature accordingly lies between approximately the boiling point of the m-dichlorobenzene as lower limit and that of the m-chlorobenzene sulphonyl chloride as upper limit, and is determined by the proportions of m-dichlorobenzene and halogenating agent in the reaction mixture. It is optionally possible to work in the presence of halogen transfer agents, for example $PCl_3$, $PCl_5$, $POCl_3$ or $COCl_2$, and/or in the presence of solvents of high boiling point, for example hexachlorobenzene or polychlorinated biphenylene.

In another similarly preferred form of the reaction, the chlorolysis is carried out in the liquid phase with ultraviolet irradiation or with addition of radical formers (c) in the temperature range of from 20° to 260° C, preferably from 50° to 210° C and more particularly from 70° to 150° C, optionally in the presence of inert diluents, for example carbon tetrachloride. Unreacted initial material and unreacted or excess or reformed chlorinating agents are recovered with (a), (b) and (c) and are reintroduced into the reaction mixture.

When carrying out the reaction in the liquid phase, the progress of the reaction is preferably monitored by gas chromatography. It may be advantageous for the formed m-dichlorobenzene to be distilled off continuously through a column from the reaction mixture. Depending on the chosen reaction temperature, this takes place at a reduced or slightly raised pressure. When distilling off m-dichlorobenzene, it is preferred to work at normal pressure.

It is extremely surprising that the process according to the invention can be carried out, since with the chlorination of benzene sulphonyl chloride in the manner similar to the known chlorination of p-chlorobenzene sulphonyl chloride, it was to be expected that there would be an exchange of the $SO_2Cl$ group for chlorine and hence the formation of chlorobenzenes (Journ. Am. Soc. 72, page 1215 (1950)). On the basis of the prior art and because of the known possibility of converting p-toluosulphonic acid chloride to 4-methyl-3-chlorobenzene sulphonyl chloride, 4-methyl-3,5-dichlorobenzene sulphonyl chloride and 4-methyl-2,3,5-trichlorobenzene sulphonyl chloride (German Pat. Nos. 133,000 and 210,856), it was to be assumed that, in the case of chlorination of the benzene sulphonyl chloride ring, the ring must be activated, at least by alkyl groups. It was not at all possible to foresee a smoothly proceeding and selective meta-chlorination of benzene sulphonyl chloride. Hitherto, m-chlorobenzene sulphonyl chloride was only obtainable with moderate yields after multi-stage processes (Journ. Org. Chem. 21, page 1382 (1956); Ber. 90, 841–852 (1957); Australian Journ. Chem. 6, pages 318–320 (1953); Rect. Trav. Chim. 84, pages 24–30 (1965)). The process according to the invention thus makes it possible for m-chlorobenzene sulphonyl chloride to be prepared in a particularly advantageous manner. Furthermore, m-dichlorobenzene can be produced on an industrial scale by a particularly simple procedure. The process is suitable for continuous operation, since it is possible in both stages for unreacted starting products and intermediate products, including the halogenation agents, to be returned to the reaction after being fractionated in continuously operated columns. The overall process accordingly proceeds in accordance with the reaction equation:

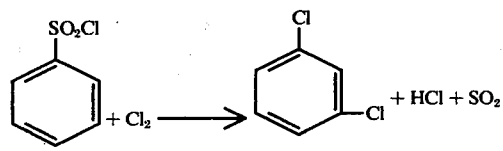

m-Chlorobenzene sulphonyl chloride and m-dichlorobenzene are valuable intermediate products for the production of plant protection agents. m-Dichlorobenzene, can, for example, be used for the production of 2,4-dichloronitrobenzene, which is used as an intermediate for the production of benzo(c)-cinnoline dyestuffs (Offenlegungsschrift No. 2,041,689).

The invention is illustrated in the following Examples.

EXAMPLE 1.

353 g (2 mols) of benzene sulphonyl chloride and 10 g of iron filings are initially placed in a conventional chlorination apparatus. Chlorine is introduced at 50° to 52° C until there is an increase in weight of 72 g. Suction-filtering is carried out, followed by washing with iced water until neutral and drying over $Na_2SO_4$.

Approximate yield 315 g (67.35% of m-chlorobenzene sulphonyl chloride, 26.85% based on starting material).

Calculated yield: 66% of the theoretical of m-chlorobenzene sulphonyl chloride. (Examples 1 to 16 illustrate the first stage of the process).

EXAMPLES 2 TO 12

177 g (1 mol) of benzene sulphonyl chloride, optionally a solvent and the indicated weight of iron fillings (catalyst) are initially supplied. The batch is saturated at room temperature with hydrogen chloride. At the indicated temperature, chlorine is introduced up to the indicated increase by weight. The substance is filtered off with suction at room temperature and separated by vacuum distillation from dissolved catalyst fractions and from difficulty volatile impurities. In the crude product which is obtained, the yield of m-chlorobenzene sulphonyl chloride is determined by gas chromatography.

| Example | Solvent ml CCl₄ | g (% by wt.) iron filings | Reaction temperature ° C | g increase in weight | Calc. conversion % | g. crude product | Calc. yield % of theoretical of m-chlorobenzenesulphonyl chloride |
| --- | --- | --- | --- | --- | --- | --- | --- |
| 2 | — | 10 (5.65) | 20 – 24 | 37 | 41 | 166.3 | 64 |
| 3 | — | 10 (5.65) | 91 – 96 | 37 | 71 | 172.4 | 67 |
| 4 | — | 10 (5.65) | 130 – 136 | 36 | 64 | 170.0 | 62.4 |
| 5 | 100 | 10 (5.65) | 46 – 53 | 35 | 83 | 189.0*⁾ | 77 |
| 6 | — | 0.34 (0.19) | 48 – 55 | 35 | 76 | 199 | 81 |
| 7 | — | 0.09 (0.05) | 49 – 56 | 9 | 9 | 186**⁾ | 80 |
| 8 | — | 10 (5.65) | 160 – 170 | 34 | 66 | 105 | 11 |
| 9 | — | 10 (5.65) | 0 | 29 | 22 | 173 | 69 |
| 10 | — | Catalyst 1.77 g Fe + 0.18 g I₂ (% by wt.) | 49 – 55 | 40 | 88 | 189 | 67 |
| 11 | — | 1.77 g Fe + 0.18 g S | 48 – 51 | 37 | 58 | 191 | 80 |
| 12 | — | 1.77 g FeCl₃ | 50 – 52 | 34 | 89 | 205 | 77 |

*) after removal of CCl₄
**) undistilled

EXAMPLE 13

706 g (4 mols) of benzene sulphonyl chloride and 10 g of iron filings are initially placed in a 2-liter stirrer-type apparatus. The mixture is saturated with gaseous hydrochloric acid and chlorine is introduced at 50° to 60° C until there is an increase in weight of 150 g. Distillation takes place after removal of the catalyst. 741 g of crude product of b.p.: 113° to 120° C/3 mm.Hg are obtained. By fine rectification, 133 g of benzene sulphonyl chloride (19% recovery) of b.p.: 89° C/1.3 mm.Hg and 572 g of m-chlorobenzene sulphonyl chloride (yield relative to reacted benzene sulphonyl chloride = 83% of the theoretical) of b.p.: 102° C/1.6 to 1.7 mm.Hg are obtained.

Further processing, see Examples 17 to 25.

EXAMPLE 14

250 g (1.41 mols) of benzene sulphonyl chloride are chlorinated with the addition of 7 g of antimony-(III)-chloride at 78° C. After an increase in weight of 51 g, 250 ml of carbon tetrachloride are added and extraction is carried out by shaking with cold concentrated hydrochloric acid. The substance is washed until neutral with water, dried and distilled.

Yield: 138 g (46.5% of the theoretical) of m-chlorobenzene sulphonyl chloride.

EXAMPLE 15

2.5 g of iodine are added to 177 g (1 mol) of benzene sulphonyl chloride. Saturation with hydrogen chloride takes place at 50° C and chlorine is introduced until there is an increase in weight of 8 g.

The yield of m-chlorobenzene sulphonyl chloride, established by gas chromatography and related to reacted starting material, amounts of 88% of the theoretical.

EXAMPLE 16

2.5 g of aluminum chloride are added to 177 g (1 mol) of benzene sulphonyl chloride. Saturation takes place at 75° C with hydrogen chloride and chlorine is introduced until the increase in weight is 10 g.

The yield of m-chlorobenzene sulphonyl chloride, relative to reacted starting material, and determined by gas chromatography, amounts to 70% of the theoretical.

EXAMPLE 17

Chlorine is introduced at 187° to 205° C into 527 g (2.5 mols) of m-chlorobenzene sulphonyl chloride and the resulting m-dichlorobenzene is continuously distilled off through a silver-jacketed column with a height of 40 cm (diameter 2.5 cm, filler bodies: glass-Raschig rings 5 × 5 mm).

Measurement by gas chromatography indicates a 93% conversion and a yield of 98% of m-dichlorobenzene, based on reacted m-chlorobenzene sulphonyl chloride.

EXAMPLE 18

424 g (2 mols) of m-chlorobenzene sulphonyl chloride and 100 ml of carbon tetrachloride are irradiated at 50° C with ultraviolet light (mercury immersion lamp), with simultaneous introduction of a stream of chlorine (8.7 g per hour). After 5¾ hours, the reaction mixture contains 15.5% of m-dichlorobenzene and 81.8% of m-chlorobenzene sulphonyl chloride. Yield: 86% of m-dichlorobenzene, based on reacted m-chlorobenzene sulphonyl chloride.

EXAMPLE 19

270 g of sulphuryl chloride are added to 424 (2 mols) of m-chlorobenzene sulphonyl chloride in 100 ml of carbon tetrachloride; at 80° C and under irradiation with ultraviolet light (mercury immersion lamp). The waste gas (sulphur dioxide and chlorine) escaping by way of a condenser still contains sulphuryl chloride. After 5½ hours, the reaction mixture contains 31.3% of m-dichlorobenzene and 67.8% of m-chlorobenzene sulphonyl chloride. Yield of m-chlorobenzene: 97% of the theoretical, based on reacted m-chlorobenzene sulphonyl chloride.

EXAMPLE 20

1414 g of m-chlorobenzene sulphonyl chloride are stirred with ultraviolet irradiation (mercury immersion lamp) at a sump temperature of 240° to 247° C. The product, boiling at 190° C, is distilled off through a silver-jacketed column (diameter 2.5 cm) with a height of 40 cm and filled with Raschig rings (5 × 5 mm). After a reaction time of 100 minutes, two fractions are obtained:

61.3 g of Fraction 1:89.9% of m-dichlorobenzene and 10.1% of chlorobenzene; and 83.1 g of Fraction 2:98.3% of m-chlorobenzene and 1.7% of chlorobenzene.

As well as 87.3% of m-chlorobenzene sulphonyl chloride, the residue (989 g) also contains 4.7% of m-dichlorobenzene.

The yield of m-dichlorobenzene amounts of 48% of the theoretical.

EXAMPLE 21

211 g (1 mol) of m-chlorobenzene sulphonyl chloride are initially provided and heated by means of an oil bath. 128.3 g (0.96 mol) of sulphuryl chloride are introduced drop-wise at a reaction temperature of from 196° to 224° C for 4½ hours and, using a 40 cm silver column (glass Haschig rings 4 × 4 mm), m-diclorobenzene is withdrawn at head temperatures of from 140° to 173° C (760 mm.Hg), and at the same time some sulphuryl chloride distils over. $SO_2$ and residual sulphuryl chloride are collected in a cooling trap.

The following is established by gas chromatography.
The residue contains 26.4 g of starting compound.
The degree of reaction is 87.4%.
100 g (78% of the introduced quantity) of sulphuryl chloride are recovered.

The yield of m-dichlorobenzene amounts to 99% of the theoretical, based on reacted starting compound.

EXAMPLE 22

The procedure according to Example 21 is followed, but 98 g (0.75 mol) of thionyl chloride are introduced dropwise within 6 hours, instead of sulphuryl chloride.
Conversion: 43.7% after 6 hours.
Yield: 85% of the theoretical of m-dichlorobenzene, based on reacted starting compound.

EXAMPLE 23

633 g (3 mols) of m-chlorobenzene sulphonyl chloride are initially provided. At 120° C and with simultaneous irradiation with a mercury immersion lamp, 270 g (2 mols) of sulphuryl chloride are introduced dropwise within 6 hours. 255 g (1.74 mols) of m-dichlorobenzene are isolated by fractional distillation from the reaction mixture, corresponding to 87% of the theoretical, based on introduced sulphuryl chloride.

EXAMPLE 24

An equimolar mixture of m-chlorobenzene sulphonyl chloride and sulphuryl chloride is introduced dropwise at 30 ml/hour through a heated quartz tube (length 50 cm, diameter 1.5 cm) which is charged with quartz beads (diameter 4 mm).

| Reaction temperature | Conversion % | Yield of m-dichlorobenzene |
|---|---|---|
| 210 | 17.8 | 99.5 |
| 330 | 49.5 | 95 |
| 360 | 78.5 | 93.5 |

EXAMPLE 25

212 g (1 mol) of m-chlorobenzene sulphonyl chloride and 50 ml of $CCl_4$ are initially provided. At 76° to 80° C, a solution of 7 g of azo-bis-isobutyronitrile in 135 g (1 mol) of sulphuryl chloride is introduced dropwise within 5 hours. Stirring takes place for a further 2½ hours until completion of the evolution of gas at 80° C.

Conversion: 97.3%
Yield: 93% of the theoretical of m-dichlorobenzene.

EXAMPLE 26

175 g (1.3 mols) of sulphuryl chloride are added at 180° to 200° C and for 3½ hours to the crude product of Example 5, without intermediate isolation of m-chlorobenzene sulphonyl chloride. Using a column, altogether 150 ml of distillate are continuously drawn off at a head temperature of 77° to 122° C. The main component is sulphuryl chloride. The residue contains 93 g of m-dichlorobenzene.

The yield, based on introduced benzene sulphonyl chloride, amounts to 63% of the theoretical.

EXAMPLE 27

175 g (1.3 mols) of sulphuryl chloride are added to the crude product of Example 6, without intermediate isolation from m-chlorobenzene sulphonyl chloride, at 110° to 120° C and with simultaneous irradiation with a mercury immersion lamp, over a period of 3 hours.

Excess sulphuryl chloride is distilled off through a 60 cm silver column (diameter 2.5 cm, filler bodies, glass Raschig rings 4 × 4 mm).

The residue (191 g) contains 27.1% of m-dichlorobenzene, 3% of benzene sulphonyl chloride and 33.0% of m-chlorobenzene sulphonyl chloride.

Calculated yield: 53% of the theoretical of m-dichlorobenzene, based on introduced or reacted benzene sulphonyl chloride and m-chlorobenzene sulphonyl chloride.

EXAMPLE 28

353 g (2 mols) of benzene sulphonyl chloride and 10 g of iron filings are initially provided, saturated at room temperature with hydrogen chloride gas and, at 48° to 57° C, chlorine is introduced until there is an increase in weight of 74 g. The product is filtered off with suction from the catalyst. After adding 400 ml of $CCl_4$, the product is washed until neutral with 4 × 100 ml of water. It is dried over $Na_2SO_4$, filtered with suction, stirred twice with on each occasion 5 g of $Al_2O_3$ and 10 g of bleaching earth, and suction-filtered each time, $CCl_4$ is distilled off at 100 mm.Hg. 175 g (1.3 mols) of sulphuryl chloride are added to the residue (291 g) at 204° to 211° C over a period of 2 hours. Simultaneously, through a 40 cm silver-jacketed column (diameter 2.5 cm, Raschig rings 4 × 4 mm), 214 g of distillate are withdrawn at a head temperature up to 138° C.

The residue contains 3 g of benzene sulphonyl chloride, 21 g of m-dichlorobenzene and 51 g of m-chlorobenzene sulphonyl chloride. 85.7 g of m-dichlorobenzene are obtained by fractional distillation from the distillate.

Total yield: 106.7 g of m-dichlorobenzene (0.73 mol), corresponding to 42% of the theoretical, based on reacted benzene sulphonyl chloride or m-chlorobenzene sulphonyl chloride, respectively.

What is claimed is:
1. Process for preparing m-chlorobenzene sulphonyl chloride which comprises reacting benzene sulphonyl chloride with chlorine in the presence of a Friedel-Crafts catalyst at a temperature of from −20° to 180° C.
2. Process of claim 1 wherein the temperature is from 10° to 150° C.
3. Process of claim 1 wherein the reaction mixture is saturated with hydrogen chloride gas.
4. Process of claim 1 wherein chlorination is carried out only up to a conversion of from 10% to 95%.
5. Process of claim 1 wherein chlorine is introduced in amounts of 1 to 5 mols per mol of benzene sulphonyl chloride reacted.

* * * * *

UNITED STATES PATENT AND TRADEMARK OFFICE
CERTIFICATE OF CORRECTION

PATENT NO. : 4,012,442
DATED : March 15, 1977
INVENTOR(S) : Heinz-Ulrich Blank et al It is certified that error appears in the above-identified patent and that said Letters Patent are hereby corrected as shown below:

[75] Inventors, line 3, delete "both of"

[56] References Cited, line 3, "Friedi-Crafts" should read
-- Friedel-Crafts --.

Column 1, line 46, after "$AlCl_3$," insert -- $AlBr_3$, --.

Column 2, line 65, "isobutylonitrile" should read
-- isobutyronitrile --.

Signed and Sealed this

Fourteenth Day of June 1977

[SEAL]

Attest:

RUTH C. MASON
*Attesting Officer*

C. MARSHALL DANN
*Commissioner of Patents and Trademarks*